United States Patent
Kuo et al.

(10) Patent No.: US 10,358,676 B2
(45) Date of Patent: Jul. 23, 2019

(54) METHODS AND KITS FOR DETECTING KAWASAKI DISEASE

(71) Applicant: Kaohsiung Chang Gung Memorial Hospital, Kaohsiung (TW)

(72) Inventors: Ho-Chang Kuo, Kaohsiung (TW); Sung-Chou Li, Kaohsiung (TW); Wen-Ching Chan, Kaohsiung (TW)

(73) Assignee: Kaohsiung Chang Gung Memorial Hospital, Kaohsiung (TW)

( * ) Notice: Subject to any disclaimer, the term of this patent is extended or adjusted under 35 U.S.C. 154(b) by 465 days.

(21) Appl. No.: 15/053,554

(22) Filed: Feb. 25, 2016

(65) Prior Publication Data

US 2016/0289764 A1 Oct. 6, 2016

Related U.S. Application Data

(60) Provisional application No. 62/142,742, filed on Apr. 3, 2015.

(51) Int. Cl.
| | | |
|---|---|---|
| *A61K 48/00* | (2006.01) | |
| *C07H 21/02* | (2006.01) | |
| *C07H 21/04* | (2006.01) | |
| *C12Q 1/6883* | (2018.01) | |
| *G16B 40/00* | (2019.01) | |
| *G16B 20/00* | (2019.01) | |

(52) U.S. Cl.
CPC ........... *C12Q 1/6883* (2013.01); *G16B 40/00* (2019.02); *C12Q 2600/158* (2013.01); *C12Q 2600/178* (2013.01); *G16B 20/00* (2019.02)

(58) Field of Classification Search
CPC .. C12N 2310/11; C12N 15/111; A61K 31/713
See application file for complete search history.

(56) References Cited

FOREIGN PATENT DOCUMENTS

| CN | 104450901 A | 3/2015 | | |
|---|---|---|---|---|
| WO | WO 2011/057003 A2 | * | 5/2011 | ......... C12N 2310/11 |

OTHER PUBLICATIONS

Rowley AH et al., "A study of cardiovascular miRNA biomarkers for Kawasaki disease" Pediatr Infect Dis J. Dec. 2014;33(12); pp. 1296-1299.

Ki Wook Yun et a., "Elevated Serum Level of MicroRNA (miRNA)-200c and miRNA-371-Sp in Children with Kawasaki Disease"; Pediatr Cardiol (2014) 35; pp. 745-752.

* cited by examiner

*Primary Examiner* — Amy H Bowman
(74) *Attorney, Agent, or Firm* — Pilloff & Passino LLP; Sean A. Passino; Rachel K. Pilloff

(57) ABSTRACT

Kits for detecting Kawasaki disease, containing an agent for sequencing or measuring the expression level of one or more of the following: miR-941, miR-182-5p and miR-183-5p are provided. Methods for detecting Kawasaki disease in a subject, comprising the identifying of one or more of the following in the subject: miR-941, miR-182-5p and miR-183-5p, are also provided.

7 Claims, 2 Drawing Sheets

Specification includes a Sequence Listing.

SEQUENCE LISTING

```
<160> NUMBER OF SEQ ID NOS: 10

<210> SEQ ID NO 1
<211> LENGTH: 22
<212> TYPE: RNA
<213> ORGANISM: Homo sapiens

<400> SEQUENCE: 1
ugucaguuug ucaaauaccc ca                                          22

<210> SEQ ID NO 2
<211> LENGTH: 24
<212> TYPE: RNA
<213> ORGANISM: Homo sapiens

<400> SEQUENCE: 2
uuuggcaaug guagaacuca cacu                                        24

<210> SEQ ID NO 3
<211> LENGTH: 22
<212> TYPE: RNA
<213> ORGANISM: Homo sapiens

<400> SEQUENCE: 3
uauggcacug guagaauuca cu                                          22

<210> SEQ ID NO 4
<211> LENGTH: 22
<212> TYPE: RNA
<213> ORGANISM: Homo sapiens

<400> SEQUENCE: 4
acuggacuug gagucagaag gc                                          22

<210> SEQ ID NO 5
<211> LENGTH: 23
<212> TYPE: RNA
<213> ORGANISM: Homo sapiens

<400> SEQUENCE: 5
uguaaacauc cuacacucuc agc                                         23

<210> SEQ ID NO 6
<211> LENGTH: 22
<212> TYPE: RNA
<213> ORGANISM: Homo sapiens

<400> SEQUENCE: 6
```

```
ucagugcacu acagaacuuu gu                                         22

<210> SEQ ID NO 7
<211> LENGTH: 21
<212> TYPE: RNA
<213> ORGANISM: Homo sapiens

<400> SEQUENCE: 7
uucacagugg cuaaguuccg c                                          21

<210> SEQ ID NO 8
<211> LENGTH: 23
<212> TYPE: RNA
<213> ORGANISM: Homo sapiens

<400> SEQUENCE: 8
cacccggcug ugugcacaug ugc                                        23

<210> SEQ ID NO 9
<211> LENGTH: 21
<212> TYPE: RNA
<213> ORGANISM: Homo sapiens

<400> SEQUENCE: 9
uaccacaggg uagaaccacg g                                          21

<210> SEQ ID NO 10
<211> LENGTH: 22
<212> TYPE: RNA
<213> ORGANISM: Homo sapiens

<400> SEQUENCE: 10
cuuucagucg gauguuuaca gc                                         22
```

METHODS AND KITS FOR DETECTING KAWASAKI DISEASE

CROSS-REFERENCE TO RELATED APPLICATION

This application claims the benefit of U.S. Application No. 62/142,742, filed on 3 Apr. 2015, the entire disclosure of which is incorporated herein by reference.

BACKGROUND OF THE INVENTION

The subject matter discussed in the background section should not be assumed to be prior art merely as a result of its mention in the background section. Similarly, a problem and the understanding of the causes of a problem mentioned in the background section should not be assumed to have been previously recognized in the prior art. The subject matter in the background section may merely represents different approaches, which in and of themselves may also be inventions.

Kawasaki disease (KD) is a pediatric disease causing inflammation of blood vessels. Although KD has been reported in all racial and ethnic groups, children of Asia-Pacific descent are primarily affected by this disease.

The earliest and most obvious symptom of KD is fever for at least five days. If left untreated, it leads to coronary artery aneurysms in approximately 20-25 percent of affected children and KD is the leading cause of acquired heart disease in young children in developed countries. The successful detection of KD within the first 10 days of fever onset followed by high dose intravenous immunoglobulin (IVIG) can greatly reduce the incidence of coronary artery lesion.

There is currently no definitive laboratory diagnostic test for KD and the diagnosis of KD is largely a clinical one, based on the American Heart Association (AHA) 2004 diagnostic criteria. These diagnosis criteria include fever over 5 days, bilateral nonsuppurative conjunctivitis, changes to the mucous membranes, indurative angioedema of the hands and feet, dysmorphous skin rashes and acute nonpurulent cervical lymphadenopathy >1.5 cm in diameter.

However, the AHA criteria is slightly different from that of Japan Circulation Society guideline, which makes the clinical diagnosis of KD perplexing. In addition, infectious diseases, such as staphylococcal or streptococcal infection, may mimic KD. It can be difficult for the clinicians to accurately diagnose KD and promptly administer IVIG to prevent coronary artery disease in the affected children.

There is an unmet need for an economical and accurate laboratory diagnostic test for KD and the present invention satisfy this and other needs.

BRIEF SUMMARY OF THE INVENTION

In one embodiment, the present invention discloses methods for detecting Kawasaki disease in a subject, comprising the steps of: measuring the expression level of miR-182-5p (SEQ ID No: 2) in the test sample of the subject, wherein a higher miR-182-5p expression in the test sample of the subject, relative to the miR-182-5p expression level in a KD-free or control sample, is indicative the subject having KD.

In another embodiment, the present invention discloses methods for detecting Kawasaki disease in a subject, comprising the step of measuring the expression level of miR-941 (SEQ ID NO: 8) in the test sample of the subject, wherein a higher miR-941 expression in the subject, relative to the miR-941 expression level in a KD-free or control sample, is indicative the subject having KD.

In yet another embodiment, the present invention also discloses methods for detecting Kawasaki disease in a subject, comprising the step of measuring the expression level of miR-183-5p (SEQ ID NO: 3) in the test sample of the subject, wherein a higher miR-183-5p expression in the test sample of the subject, relative to the miR-183-5p expression level in a KD-free or control sample, is indicative the subject having KD.

According to some embodiments of the present invention, methods for detecting Kawasaki disease in a subject are provided, comprising the step of measuring the expression level of at least one of the following miRNAs in the test sample of the subject: miR-182-5p, miR-183-5p or miR-941, wherein a higher expression level of at least one of the following miRNAs miR-182-5p, miR-183-5p or miR-941 in the test sample, relative to the expression level of corresponding miRNA in a KD-free or control sample, is indicative of the subject having KD.

According to one embodiment, methods for detecting Kawasaki disease in a subject are provided, comprises the step of measuring the expression levels of at least two of the following miRNAs in the test sample of the subject: miR-182-5p; miR-183-5p; or miR-941, wherein higher miRNA expression levels of at least two of the following miRNAs in the test sample, relative to the expression levels of corresponding miRNAs in a KD-free or control sample, is indicative of the subject having KD.

The present invention also discloses kits for detecting Kawasaki disease in a subject, comprising an agent for sequencing or measuring the expression level of at least one of the following miRNAs in a test sample: miR-941, miR-182-5p or miR-183-5p. In one embodiment, the kit further comprises a label indicates that the agent for measuring miRNA is for detecting Kawasaki disease.

Also provided are agents for sequencing or measuring the expression level of at least one of the following miRNAs in the manufacture of a kit for detecting KW in a subject: miR-941, miR-182-5p or miR-183-5p.

In another exemplary embodiment, methods for establishing a KD-specific machine learning algorithms are provided, comprising: (a) determining the ΔCt value of at least one of the following miRNAs: miR-223-3p (SEQ ID NO: 1), miR-182-5p (SEQ ID NO: 2), miR-183-5p (SEQ ID NO: 3), miR-378a-3p ((SEQ ID NO: 4), miR-30c-5p (SEQ ID NO: 5), miR-148a-3p (SEQ ID NO: 6), miR-27a-3p (SEQ ID NO: 7), miR-941 (SEQ ID NO: 8), miR-140-3p (SEQ ID NO: 9) or miR-30e-3p (SEQ ID NO: 10) from a reference pool of subjects without Kawasaki Disease and a reference pool of subjects having Kawasaki disease; and (b) registering at least one of the ΔCt value from a reference pool of the subjects without Kawasaki Disease and at least one ΔCt value from a reference pool of the subjects with Kawasaki Disease from step (a) into a machine learning algorithm, (c) establishing a binary classification model using the machine learning algorithm from step (b).

In yet another exemplary embodiment, methods are provided for diagnosing Kawasaki Disease using the KD-specific machine learning algorithms described herein.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF THE DRAWINGS

Illustrative embodiments of the present invention are described in detail below with reference to the following Figures.

DETAILED DESCRIPTION OF THE INVENTION

Figure 1:
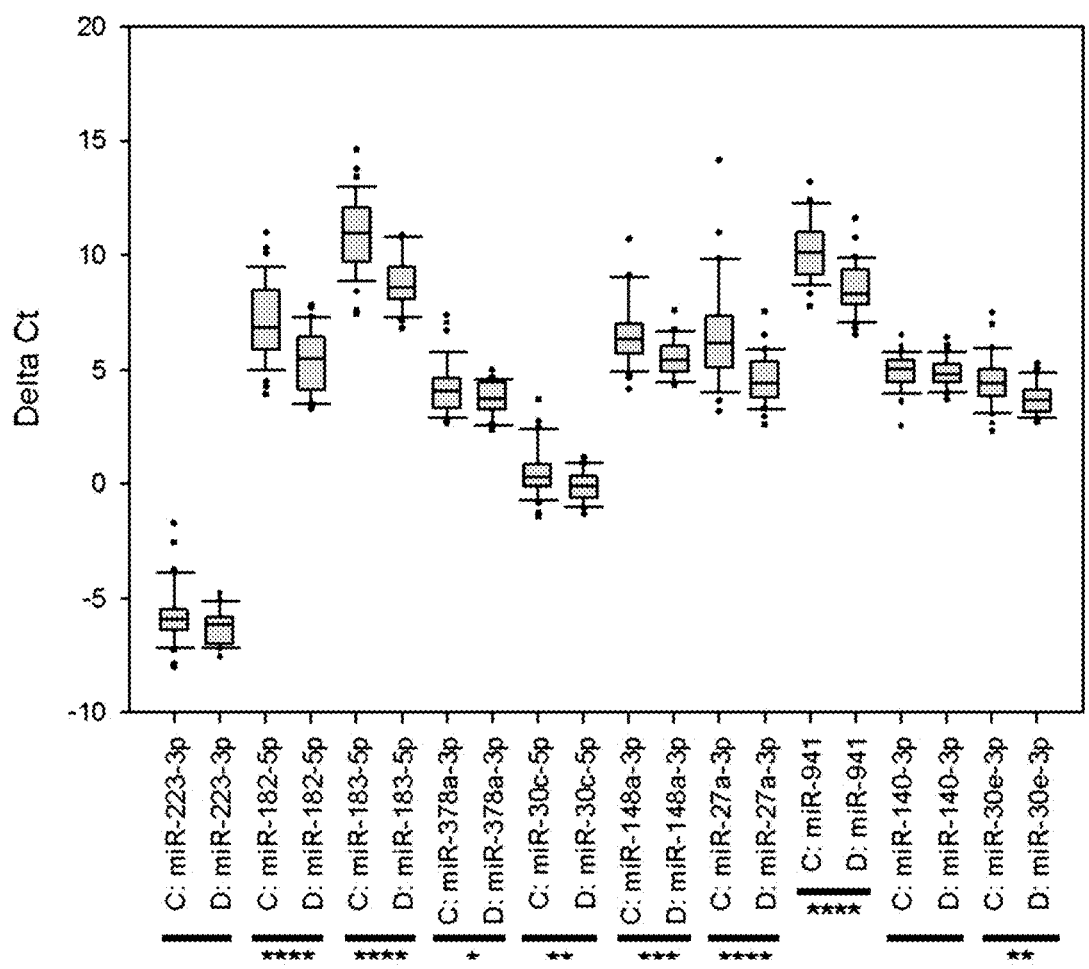
FIG. 1 is a bar graph illustrating the expression levels ($\Delta$Ct) of ten miRNAs: miR-223-3p, miR-182-5p, miR-183-5p, miR-378a-3p, miR-30c-5p, miR-148a-3p, miR-27a-3p, miR-941, miR-140-3p or miR-30e-3p in 31 febrile control samples (labelled as "C" on the X-axis) and 37 KD samples (labelled as "D" on the X-axis), using qPCR analysis. "**", "*", "**" and "*" denote $p<0.0001$, $p<0.001$, $p<0.01$ and $p<0.05$, respectively.

As used herein, the articles "a" and "an" refer to one or more than one (i.e., at least one) of the grammatical object of the article.

The term "subject" may refer to a vertebrate suspected of having KD. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.).

As used herein interchangeably, a "microRNA," "miR," or "miRNA" refers to the unprocessed (e.g., precursor) or processed (e.g., mature) RNA transcript from a miR gene. MicroRNAs are endogenous non-coding single-stranded RNAs of approximately 22 nucleotides in length and constitute a novel class of gene regulators (Chua, et al. (2009) Curr. Opin. Mol. Ther. 11:189-199).

All numbers herein may be understood as modified by "about."

Methods for Diagnosing Kawasaki Disease

The present invention is based, in part, on the identification of particular miRNA whose expression level is increased in a test sample, relative to the predetermined level of the corresponding miRNA in a KD-free sample. Some embodiments of the present invention are directed to methods of diagnosing whether a subject has, or is at risk for developing, KD, comprising measuring the expression level of at least one miR in a test sample from the subject and comparing the expression level of the corresponding miR in the KD-free or control sample, wherein a higher miRNA expression level in the test sample, relative to that of the control sample, is indicative of the subject having KD.

The predetermined miRNA expression level in a KD-free or control sample is from a representative pool of KD-free individuals, and are a mean, median or other statistically manipulated or otherwise summarized or aggregated representative miRNA expression level in the KD-free or control samples.

A higher miRNA expression is a relative term and can be determined by comparison of the miRNA expression level in the test sample to that from a referenced pool of subjects known to be KD-free. In some embodiments, the expression of miRNA level in a test sample is 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 350%, 400%, 450%, 500% higher than that from a referenced pool of subject known to be KD-free.

In one embodiment, the expression level of at least one of the following miRNAs is measured in the test sample of a subject to diagnose KD: miR-223-3p, miR-182-5p, miR-183-5p, miR-378a-3p, miR-30c-5p, miR-148a-3p, miR-27a-3p, miR-941, miR-140-3p, or miR-30e-3p.

In another embodiment, the expression level of one or more of the following miRNAs is measured in the test sample of subject to diagnose KD: miR-182-5p, miR-183-5p or miR-941.

In one exemplary embodiment, the expression level of miR-182-5p is measured in the test sample of a subject for KD diagnosis. In another exemplary embodiment, the expression level of miR-183-5p is measured in the test sample of a subject for KD diagnosis. In yet another exemplary embodiment, the expression level of miR-941 is measured in the test sample of a subject for KD diagnosis.

In yet another embodiment, the expression levels of two or more of the following miRNAs are measured in the test sample of a subject to diagnose KD: miR-223-3p, miR-182-5p, miR-183-5p, miR-378a-3p, miR-30c-5p, miR-148a-3p, miR-27a-3p, miR-941, miR-140-3p or miR-30e-3p In some embodiments, the expression of one of more of the following miRNAs are measured in the test sample of a subject to diagnose KD miR-27a-3p; miR-148a-3p; miR-30c-5p, miR-30e-3p; miR-378a-3p; miR-233-3p or miR-140-3p.

In one exemplary embodiment, the expression levels of miR-182-5p and miR-183-5p are measured in the test sample of a subject for KD diagnosis. In another exemplary embodiment, the expression levels of miR-182-5p and miR-941 are measured in the test sample of a subject for KD diagnosis. In yet another exemplary embodiment, the expression levels of miR-183-5p and miR-941 are measured in the test sample of a subject for KD diagnosis. In yet another exemplary embodiment, the expression levels of miR-182-5p, miR-183-5p and miR-941 are measured in the test sample of a subject for KD diagnosis. In some embodiments, the combination of two or more miRNA expression level offer a higher accuracy, sensitivity or specificity for KD diagnosis.

Measuring the level of miRNA expression refers to quantifying the amount of miRNA present in a sample. Measuring the expression level of a specific, or any miRNA, can be achieved using any method known in the art or described herein, such as by real-time PCR, Northern blot analysis, or other techniques well known to those of skill in the art. Measuring the expression level of miRNA includes measuring the expression of either a mature form of miRNA or a precursor form that is correlated with miRNA expression.

In a particular embodiment, the level of at least one miRNA is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

In some embodiments, use of a microarray is desirable. A microarray is a microscopic, ordered array of nucleic acids, proteins, small molecules, cells or other substances that enables parallel analysis of complex biochemical samples. Microarrays can be fabricated using a variety of technologies, including printing with fine-pointed pins onto glass slides, photolithography using pre-made masks, photolithography using dynamic micromirror devices, ink jet printing, or electrochemistry on microelectrode arrays.

Microarray analysis of miRNAs, for example, can be accomplished according to any method known in the art. In one embodiment, RNA is extracted from a cell or a sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In one embodiment, the microarray comprises miRNA-specific probe oligonucleotides for sequencing or measuring miRNAs selected the group consisting of: miR-223-3p, miR-182-5p, miR-183-5p, miR-378a-3p, miR-30c-5p, miR-148a-3p, miR-27a-3p, miR-941, miR-140-3p, miR-30e-3p or the combination thereof.

In some embodiments, use of quantitative RT-PCR is desirable. Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miRNA, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, include, but are not limited to, via agarose gel electrophoresis, the use of SYBR Green (a double stranded DNA dye), and the use of a fluorescent reporter probe.

The identification of miRNAs that are differentially expressed in KD and non-KD subjects, allows the use of this information in a number of ways. For example, a particular treatment regime may be evaluated (e.g., to determine whether a therapy is effective to prevent the coronary artery complications in a subject with KD). Similarly, diagnosis may be done or confirmed by comparing the miRNA expression level in a test sample with known expression profiles from non-KD samples. Furthermore, these miRNA expression profiles allow screening of drug candidates that suppress miRNA expression in KD, or convert a poor prognosis profile to a better prognosis profile.

In one exemplary embodiment, methods for establishing KD-specific machine learning algorithms are provided, comprising: (a) determining the ΔCt value of at least one of the following miRNAs: miR-223-3p, miR-182-5p, miR-183-5p, miR-378a-3p, miR-30c-5p, miR-148a-3p, miR-27a-3p, miR-941, miR-140-3p or miR-30e-3p from a reference pool of subjects without Kawasaki Disease and a reference pool of subjects having Kawasaki disease; and (b) registering at least one ΔCt values from the reference pool of subjects without Kawasaki Disease and at least one ΔCt values from the reference pool of subjects with Kawasaki Disease from step (a) into a machine learning algorithm; and (c) establishing a binary classification model using the machine learning algorithm in step (b).

In another embodiment, methods of diagnosing KD are provided, comprising: (a) determining the ΔCt value of at least two of the following miRNAs: miR-223-3p, miR-182-5p, miR-183-5p, miR-378a-3p, miR-30c-5p, miR-148a-3p, miR-27a-3p, miR-941, miR-140-3p or miR-30e-3p from a test sample; and (b) registering one or more of the ΔCt values from step (a) into a KD-specific machine learning algorithm described herein.

Non limiting examples of machine learning network include Support Vector Machines (SVM), artificial neural networks, decision tree learning (e.g, CART, ID3, C4.5, CHAID, MARS, and Conditional Inference Trees), instance based learning (e.g, K-Nearest Neighbor), Bayesian networks, genetic algorithms and ensemble learning (e.g., Bagging and Boosting).

In an exemplary embodiment, methods of diagnosing KD are provided, comprising: (a) determining the ΔCt value of at least one of the following miRNAs: miR-182-5p; miR-183-5p; miR-941 from a test sample; and (b) registering one or more of the ΔCt values from step (a) into a KD-specific machine learning algorithm described herein. In one embodiment, the machine learning algorithm is Support Vector Machines (SVM).

Kits for Diagnosing Kawasaki Disease

The present invention also provides kits for use in diagnosing KD. The kit comprises an agent for sequencing or measuring the expression level of one or more of the following miRNAs: miR-223-3p, miR-182-5p, miR-183-5p, miR-378a-3p, miR-30c-5p, miR-148a-3p, miR-27a-3p, miR-941, miR-140-3p or miR-30e-3p in a test sample.

KD is diagnosed using the kit if the miRNA expression level in the test sample is higher, relative to the expression level of corresponding miRNA in a KD-free sample. Non limiting examples of the test sample include body fluid (e.g. serum, blood, effusion) and tissue.

In one embodiment, the kit further comprises an instruction for KD diagnosis. In another embodiment, the agent is RT-PCR. In another embodiment, the agent is a probe oligonucleotide specific for sequencing or measuring SEQ ID NO: 1 to SEQ ID NO: 10 miRNAs. The agent can be an agent known in the art for measuring the expression level of a specific, or any miRNA.

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated. Some of the procedures are described below for illustrative purpose.

Description of Materials and Methods Used in the Examples

Whole blood samples were collected from patients diagnosed with KD or without KD (fever control or "FC") in Kaohsiung Chang Gung Memorial Hospital, Taiwan. The clinical diagnosis of KD by physicians was considered as the gold standard for this study. FC are patients with fever for >5 days but do not have KD.

31 KD and 37 FC subjects were enrolled in the training group and 19 KD and 33 FC subjects were enrolled in the blind test group. 30% of the KD patients had positive coronary artery lesions. The red blood cells in the collected blood samples were depleted or removed. The RNA in the remaining white blood cell (WBC) portion was extracted using the mirVana miRNA isolation kit (Life technology, CA, USA), and further processed by either NGS or real-time PCR (qPCR) assays.

Results miRNA Expression Profile by NGS

12 FC WBC samples and 12 KD WBC samples were randomly selected from the training group and the extracted RNA were pooled to form four RNA libraries (two KD pooled RNA libraries and two FC pooled RNA libraries). The pooled libraries were prepared with TruSeq® Small RNA (Illumina) sample preparation protocol, then sequenced with the next generation sequencing (NGS) platform, acquiring more than 5 millions of sequence reads for each library. The initial sequence reads in fastq format were analyzed with miRSeq (CT Pan et al., A User-Friendly Standalone Toolkit for Sequencing Quality Evaluation and miRNA Profiling. Biomed Res Int 2014; 2014:462135) for evaluating overall sequencing qualities and determining miRNA expression profiles, which showed that the NGS data was of high quality and consistent. The majority of the reads with 3' adaptor detected and trimmed was 22-nt long, which implied that most (more than 80%) of the analyzed sequence reads belonged to miRNAs genes.

A clustering analysis was conducted to examine whether the FC and KD samples were distinguishable based on miRNA expression profiles. The heatmap image showed that more than 20 hsa-miRNAs were differentially expressed in FC and KD samples (higher in the KD samples) and 10 of them were selected for further qPCR validation.

qPCR Validation

The TaqMan® MicroRNA Transcription Kit (Life technologies) was used to prepare cDNA. Reverse-transcription reactions were performed on a Veriti 96 well thermal cycler (Life Technologies) in accordance with the manufacturers' instructions. Reverse-transcription product was diluted 10 folds and 5 µl of the diluted product was used for qPCR reaction. Quantitative RT-PCR was carried out using the 7500 Real-Time PCR System (Life technologies) and the TaqMan Universal PCR Master Mix II without UNG (Life Technologies). Real-time PCR cycling conditions were: 95° C. for 10 min followed by 40 cycles of 95° C. for 15s and 60° C. for 1 min. MicroRNA expression abundances were determined by the $\Delta Ct$ values using a small nucleolar RNA U6 as the endogenous control.

qPCR validation showed 10 miRNAs expression levels were consistent with that of NGS. As illustrated in FIG. 1, $\Delta Ct$ of eight miRNAs were differentially expressed between KD samples and non-KD samples (p values):

1. hsa-miR-182-5p, hsa-miR-183-5p, hsa-miR-941 and hsa-miR-27a-3p ($p<0.0001$);
2. hsa-miR-148a-3p ($p<0.001$);
3. hsa-miR-30c-5p and hsa-miR-30e-3p ($p<0.01$); and
4. hsa-miR-378a-3p ($p<0.05$).

Although the expression levels of hsa-miR-233-3p and hsa-miR-140-3p were not significantly different between KD and fever control groups, a trend of differential expression (lower $\Delta Ct$ in KD samples compare to that of control samples) was observed (see FIG. 1).

The Performance of the KD Specific SVM Alignment Model

Figure 2:
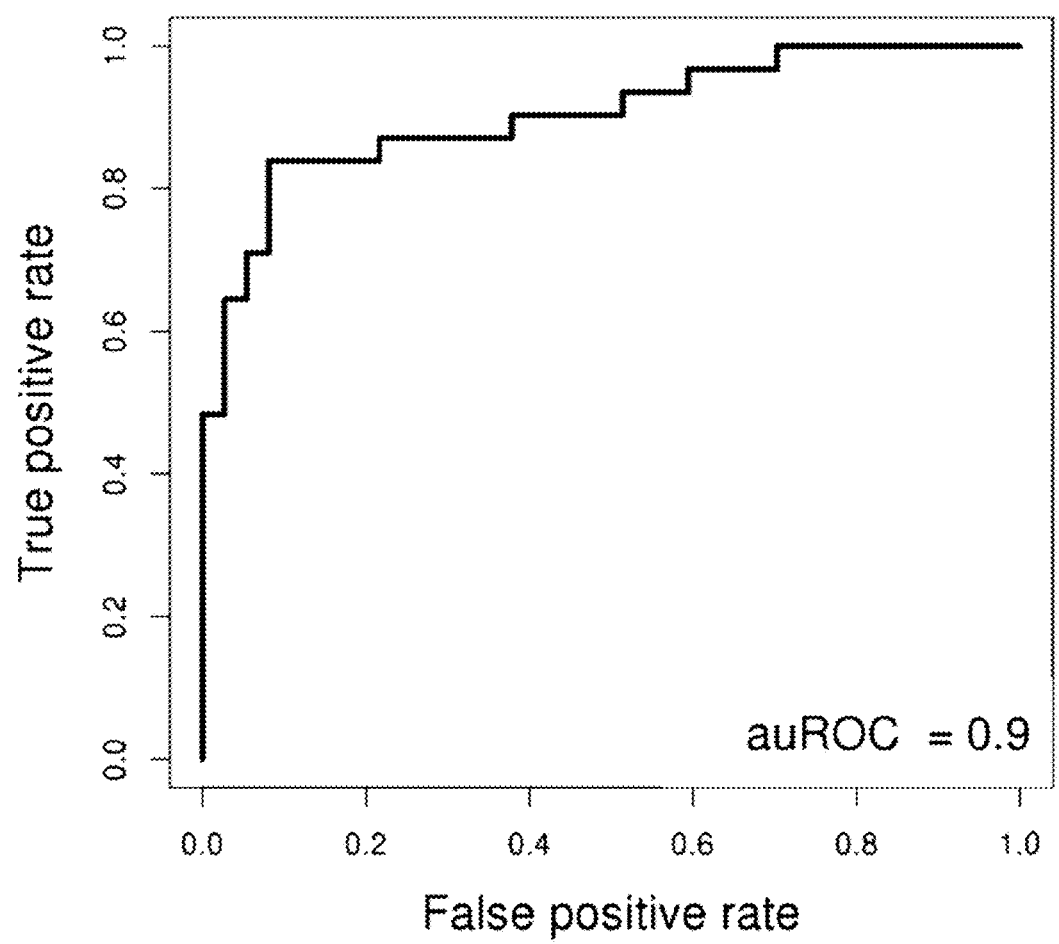
FIG. 2 is an ROC curve of the support vector machines (SVM) classification model based on the 10 miRNAs expression levels ($\Delta$Ct) in FIG. 1.

The libsvm module of the support vector machines (SVM) was used to develop a KD specific SVM alignment model to discriminate FC and KD samples based on the miRNA expression. The $\Delta Ct$ (threshold cycle) values of the 10 miRNAs from the 37 FC and 31 KD samples were used to develop a KD-specific SVM alignment and 5-fold cross validation policy was adopted to eliminate overfitting and underfitting. The $\Delta Ct$ values of 10 miRNAs (miR-223-3p, miR-182-5p, miR-183-5p, miR-378a-3p, miR-30c-5p, miR-148a-3p, miR-27a-3p, miR-941, miR-140-3p and miR-30e-3p) were weighted and computed to calculate a total score using the SVM alignment model. The total score was between 0 to 1. If the total score is larger than or equal to 0.5, it is classified as a POSITIVE case (KD) whereas a total score less than 0.5 is classified as a NEGATIVE case (FC). As illustrated in FIG. 2, the final SVM alignment model for diagnosing KD has an 83.3% sensitivity and an 92.5% specificity, leading to an 87.9% overall accuracy. In addition, the auROC value is up to 0.9.

An independent blind test was performed on an independent cohort, which comprises 33 FC and 19 KD subjects. RNA were extracted from the collected blood samples based on the protocol described above and the miRNA expression profile was analyzed with qR-T PCR. After KD specific SVM model alignment, 16 out of the 19 KD samples were diagnoses as KD; 27 out of the 33 FC samples were diagnosed as not KD, resulting in six false positives. Therefore, the blind test demonstrated a 84.20% sensitivity and a 81.8% specificity, leading to an 82.7% overall accuracy based on the $\Delta Ct$ values of the 10 miRNAs measured, when compare with the KD diagnosis by physician (the gold standard).

TABLE 2

|  |  | Diagnosis by miRNAs | | |
|---|---|---|---|---|
|  |  | Positive | Negative | Sum |
| Diagnosis by physician | Positive | 16 | 3 | 19 |
|  | Negative | 6 | 27 | 33 |
|  | Sum | 22 | 30 |  |

The KD-specific SVM alignment model derived from above was used to calculate the sensitivity, specific and accuracy of miR-182-5p, miR-183-5p and miR-941, alone or in combination, based on the $\Delta Ct$ of these miRNAs. The results are shown in Table 3.

TABLE 3

The sensitivity, specificity and accuracy of hsa-miR-182-5p, hsa-miR-183-5p and hsa-miR-941 in KD diagnosis.

| miRNA | Sensitivity | Specificity | Accuracy |
|---|---|---|---|
| hsa-miR-182-5p | 58.57% | 78.21% | 69.16% |
| hsa-miR-183-5p | 75.71% | 83.93% | 79.91% |
| hsa-miR-941 | 67.14% | 73.93% | 70.81% |
| hsa-miR-182-5p + hsa-miR-183-5p | 90.48% | 72.50% | 80.63% |
| hsa-miR-182-5p + hsa-miR-941 | 68.10% | 81.79% | 75.22% |
| hsa-miR-183-5p + hsa-miR-941 | 71.9% | 77.86% | 74.98% |
| hsa-miR-182-5p + hsa-miR-183-5p + hsa-miR-941 | 74.29% | 87.14% | 80.85% |

The results show the accuracy for miR-182-5p in KD diagnosis is 69.16% and for miR-941 in KD diagnosis is 70.81%. In contrast, the accuracy for miR-182-5p and miR-941 combination in KD detection increased to 75.22%.

The sensitivity for miR-183-5p in KD diagnosis is 75.71% and for miR-182-5P in KD diagnosis is 58.57%. In contrast, the sensitivity for miR-182-5p and miR-183-59 combination in KD detection increased to 90.48%.

The specificity for miR-182-5P in KD diagnosis is, 78.21%, for miR-183-5p in KD diagnosis is 83.93% and for miR-941 in KD diagnosis is 73.93%. In contrast, the specificity for miR-182-5p, miR-183-59 and miR-941 combination in KD detection increased to 87.14%.

What is claimed is:

1. A method for detecting and treating Kawasaki disease in a subject, comprising
   (a) measuring the expression levels of at least one of the following miRNAs in the test sample of the subject: miR-182-5p, miR-183-5p or miR-941, wherein higher expression levels of at least one of the miRNAs in the test sample, relative to the expression levels of corresponding miRNAs in a Kawasaki disease-free sample, is indicative of the subject having Kawasaki disease; and
   (b) administering an effective amount of high dose intravenous immunoglobulin (IVIG) to the subjected diagnosed with Kawasaki disease.

2. The method of claim 1, wherein the miRNA is at least one of miR-182-5p and miR-183-5p.

3. The method of claim 1, wherein the miRNA is at least one of miR-183-5p and miR-941.

4. The method of claim 1, wherein the miRNA is at least one of miR-182-5p and miR-941.

5. The method of claim 1, wherein the miRNAs is at least one of miR-182-5p, miR-183-5p and miR-941.

6. The method of claim 1, further comprising the step of measuring at least one of the following miRNAs: miR-27a-3p; miR-148a-3p; miR-30c-5p, miR-30e-3p; miR-378a-3p; miR-233-3p or hsa-miR-140-3p.

7. The method of claim 1, wherein the miRNA expression level is determined by real-time PCR.

* * * * *